US012758782B2

(12) United States Patent
Young et al.

(10) Patent No.: US 12,758,782 B2
(45) Date of Patent: Oct. 13, 2026

(54) IMPLANTABLE MEDICAL DEVICE CONFIGURED TO PROVIDE AN INTRACARDIAC FUNCTION

(71) Applicant: BIOTRONIK SE & Co. KG, Berlin (DE)

(72) Inventors: Daniel Young, Portland, OR (US); Madeline Anne Midgett, Portland, OR (US); Christopher Jones, Oregon City, OR (US); R. Hollis Whittington, Portland, OR (US)

(73) Assignee: I BIOTRONIK SE & Co. KG, Berlin (DE)

( * ) Notice: Subject to any disclaimer, the term of this patent is extended or adjusted under 35 U.S.C. 154(b) by 181 days.

(21) Appl. No.: 18/557,078

(22) PCT Filed: Apr. 26, 2022

(86) PCT No.: PCT/EP2022/060957

§ 371 (c)(1),
(2) Date: Oct. 25, 2023

(87) PCT Pub. No.: WO2022/233634

PCT Pub. Date: Nov. 10, 2022

(65) Prior Publication Data

US 2024/0207619 A1 Jun. 27, 2024

Related U.S. Application Data

(60) Provisional application No. 63/184,494, filed on May 5, 2021.

(30) Foreign Application Priority Data

Jun. 7, 2021 (EP) .................................... 21177962

(51) Int. Cl.
*A61N 1/365* (2006.01)
*A61N 1/05* (2006.01)
(Continued)

(52) U.S. Cl.
CPC ......... *A61N 1/365* (2013.01); *A61N 1/37512* (2017.08); *A61N 1/3756* (2013.01); *A61N 1/0573* (2013.01)

(58) Field of Classification Search
CPC .. A61N 1/365; A61N 1/37512; A61N 1/3756; A61N 1/0573; A61N 1/36507;
(Continued)

(56) References Cited

U.S. PATENT DOCUMENTS 5,562,709 A * 10/1996 White .................. A61N 1/3621 600/518
2017/0368360 A1* 12/2017 Hahn ................ A61N 1/36514
(Continued)

FOREIGN PATENT DOCUMENTS

EP 3209376 B1 10/2018
JP 2019519326 A 7/2019

OTHER PUBLICATIONS

European Search Report mailed on Nov. 25, 2021, by the European Patent Office for Application No. EP21177962.4. (8 pages).
(Continued)

*Primary Examiner* — Brian T Gedeon
(74) *Attorney, Agent, or Firm* — Buchanan Ingersoll & Rooney PC

(57) ABSTRACT

An implantable medical device configured to provide for an intracardiac function comprises a body, a sensor arrangement arranged on the body and configured to receive a cardiac sense signal, and a processing circuitry operatively connected to the sensor arrangement. The processing circuitry is configured to process the cardiac sense signal
(Continued)

received using the sensor arrangement to monitor the cardiac sense signal to detect whether a start criterion is fulfilled, wherein the start criterion is fulfilled if at least one signal sample (s(i−3) . . . s(i+3)) of the cardiac sense signal is smaller than a start threshold, and to start an atrial detection window for detecting, within the atrial detection window, a signal deflection of the cardiac sense signal potentially indicative of an atrial event, based on whether the detection criterion is fulfilled.

13 Claims, 6 Drawing Sheets

(51) Int. Cl.
*A61N 1/368* (2006.01)
*A61N 1/375* (2006.01)

(58) Field of Classification Search
CPC ... A61N 1/36514; A61N 1/3682; A61B 5/346
See application file for complete search history.

(56) References Cited

U.S. PATENT DOCUMENTS

| | | | |
|---|---|---|---|
| 2018/0021581 | A1 | 1/2018 | An et al. |
| 2018/0028814 | A1 | 2/2018 | Ghosh |
| 2018/0085589 | A1 | 3/2018 | Splett et al. |
| 2020/0094061 | A1 | 3/2020 | Ghosh |

OTHER PUBLICATIONS

International Search Report (PCT/ISA/210) and Written Opinion (PCT/ISA/237) mailed on Jul. 11, 2022, by the European Patent Office as the International Searching Authority for International Application No. PCT/EP2022/060957. (15 pages).

1 Japanese Office Action for Japanese Patent Application No. 2023-557130 dated Apr. 27, 2026.

* cited by examiner

IMPLANTABLE MEDICAL DEVICE CONFIGURED TO PROVIDE AN INTRACARDIAC FUNCTION

CROSS-REFERENCE TO RELATED APPLICATIONS

This application is the United States National Phase under 35 U.S.C. § 371 of PCT International Patent Application No. PCT/EP2022/060957, filed on Apr. 26, 2022, which claims the benefit of European Patent Application No. 21177962.4, filed on Jun. 7, 2021, and U.S. Provisional Patent Application No. 63/184,494, filed on May 5, 2021, the disclosures of which are hereby incorporated by reference herein in their entireties.

TECHNICAL FIELD

The present invention generally relates to an implantable medical device for providing an intracardiac function, in particular, a pacing function such as ventricular pacing, specifically VDD pacing.

BACKGROUND

In an implantable medical device, e.g., in the shape of a leadless pacemaker device or a cardiac stimulation device using a subcutaneously implanted pulse generator and one or multiple leads extending into a patient's heart, it may be desirous to provide stimulation in a ventricle of the patient's heart, e.g., in the right ventricle, in synchrony with atrial activity. For this, ventricular pacing shall take into account atrial sense signals to control the ventricular pacing based on atrial events indicative of atrial activity, for example in a so-called VDD pacing mode.

In recent years, leadless pacemakers have received increasing attention. Leadless pacemakers, in contrast to pacemakers implanted subcutaneously using leads extending transvenously into the heart, avoid leads in that the pacemaker device itself is implanted into the heart, the pacemaker having the shape of a capsule for implantation into cardiac tissue, in particular the right ventricle. Such leadless pacemakers exhibit the inherent advantage of not using leads, which can reduce risks for the patient involved with leads transvenously accessing the heart, such as the risk of pneumothorax, lead dislodgement, cardiac perforation, venous thrombosis and the like.

A leadless pacemaker or a lead of a stimulation device may specifically be designed for implantation in the right ventricle and, in this case, during implant is placed e.g., in the vicinity of the apex of the right ventricle. Ventricular pacing may, for example, be indicated in case a dysfunction at the AV node occurs, but the sinus node function is intact and appropriate. In such a case in particular a so-called VDD pacing may be desired, involving a ventricular pacing with atrial tracking and hence requiring a sensing of atrial activity in order to a pace at the ventricle based on intrinsic atrial contractions.

A VDD pacing is in particular motivated by patient hemodynamic benefits of atrioventricular (AV) synchrony by utilizing an appropriate sinus node function to trigger ventricular pacing, potentially allowing to maximize ventricular preload, to limit AV valve regurgitation, to maintain low mean atrial pressure, and to regulate autonomic and neurohumoral reflexes.

Publications have explored solutions to use modalities to detect mechanical events of atrial contractions, including the sensing of motion, sound and pressure (see, for example, U.S. Publication No. 2018/0021581 A1 disclosing a leadless cardiac pacemaker including a pressure sensor and/or an accelerometer to determine an atrial contraction timing). As mechanical events generally exhibit a small signal amplitude, signal detection based on mechanical events, for example motion, sound or pressure, may be difficult to sense, in particular when the implantable medical device is placed in the ventricle and hence rather far removed from the atrium of which contractions shall be sensed. In addition, wall motion and movement of blood generated by atrial contractions may not be directly translated to the ventricle, and cardiac hemodynamic signals, such as motion, heart sounds and pressure, are likely affected by external factors such as posture and patient activity.

The present disclosure is directed toward overcoming one or more of the above-mentioned problems, though not necessarily limited to embodiments that do.

SUMMARY

It is an objective to provide an implantable medical device and a method for operating an implantable medical device allowing, in particular, for ventricular pacing with atrioventricular synchrony, hence requiring a reliable sensing of atrial events in order to provide for a ventricular pacing based on such atrial events.

Such desires are addressed by an implantable medical device configured to provide for an intracardiac function having the features of claim 1.

In one aspect, an implantable medical device configured to provide for an intracardiac function comprises a body, a sensor arrangement on the body and configured to receive a cardiac sense signal, and a processing circuitry operatively connected to the sensor arrangement. The processing circuitry is configured to process the cardiac sense signal received using the sensor arrangement to monitor the cardiac sense signal to detect whether a start criterion is fulfilled, wherein the start criterion is fulfilled if at least one signal sample of the cardiac sense signal is smaller than a start threshold, and to start an atrial detection window for detecting, within the atrial detection window, a signal deflection of the cardiac sense signal potentially indicative of an atrial event, based on whether said start criterion is fulfilled.

The start criterion can also be or replaced by a sense detection criterion. In this case the atrial detection window allows monitoring of the signal for sense detections. Thus, in this case this criterion seems to be a detection criterion and not the start criterion.

Generally, the detection of an atrial event shall take place in an atrial detection window, wherein for detecting an atrial event signal deflection of the cardiac sense signal in the atrial detection window are monitored and processed in order to identify whether an atrial event may be present. Herein, if the implantable medical device is implanted in the ventricle of the patient's heart, for example in the right ventricle, signals relating to atrial activity occur in the far field, whereas ventricular signals relating to ventricular activity are received in the near field. This causes atrial signals to generally be small and noisy in comparison to ventricular signals, such that it may be hard to discern atrial signals from ventricular signals.

In particular, signal portions relating to atrial activity may be corrupted by signals originating from ventricular activity. For example, an ending of a T wave, relating to a repolarization of the ventricle after a prior QRS waveform in an intracardiac electrogram, may extend into the atrial detection window, such that portions of the T wave may falsely be identified as an atrial event in an intracardiac electrogram signal. In addition, the atrial detection window may extend into the beginning of a subsequent ventricular waveform, in particular the QRS waveform in an intracardiac electrogram signal, such that a peak amplitude for an atrial event may not be easily determined if the atrial event is identified close to a subsequent ventricular event.

Hence, to be able to identify an atrial event correctly and in particular without corruption due to a preceding waveform not relating to atrial activity (such as a T wave in an intracardiac electrogram), it herein is proposed to dynamically set the atrial detection window based on signal monitoring. In particular, the atrial detection window shall only be started once a start criterion is fulfilled. For the start criterion, it is monitored whether at least one sample of the cardiac sense signal is smaller than a start threshold, and only if this is found the atrial detection window is started.

It hence is monitored whether a prior waveform, for example a T wave in an intracardiac electrogram signal, has sufficiently decayed such that an atrial event may be reliably detected in the atrial detection window without corruption of signal portions relating to prior non-atrial signal waveforms. As the atrial event is detected based on signal deflections resulting from activity in the far field, signal deflections relating to the atrial event generally have a small amplitude and may be noisy. By starting the atrial detection window only once a start criterion is fulfilled, it may be made sure that the atrial detection window covers a portion of the cardiac sense signal which likely relates only to atrial activity, hence improving the reliability of detection of atrial events and reducing the risk of atrial undersensing, which potentially may lead to a loss of atrioventricular (AV) synchrony.

In particular, by adaptively starting the atrial detection window based on a start criterion which monitors the amplitude of the cardiac sense signal prior to the atrial detection window, false detections of an atrial event due to signal portions reaching into the atrial detection window and not relating to atrial activity may be avoided, hence improving the reliability of an atrial capture.

The sensor arrangement in particular may be formed by an electrode arrangement of one or multiple electrodes arranged on the body. Hence, by means of the sensor arrangement electrical signals may be received, such electrical signals representing intracardiac electrogram (IEGM) recordings and hence being indicative of cardiac activity.

In another embodiment, the sensor arrangement may be configured for sensing cardiac sense signals in the shape of pressure signals, acoustic signals, ultrasound signals, motion signals, and/or impedance signals.

In one embodiment, the body of the implantable medical device may be formed by a lead which is connectable to a generator of the implantable medical device. In this case, the generator may be implanted into a patient, for example subcutaneously remote from the heart, the lead forming the body extending from the generator into the heart such that the body with the sensor arrangement arranged thereon is placed in the heart, for example within the right ventricle in order to engage with tissue at the right ventricle.

In another embodiment, the body may be formed by a housing of a leadless pacemaker device. In this case, the implantable medical device is formed as a leadless device, which does not comprise leads extending from a location outside of the heart into the heart for providing for a stimulation and/or sensing within the heart. The housing of the leadless pacemaker device may be placed on tissue with a distal end formed by the housing, the sensor arrangement e.g., being placed (at least in part) on or in the vicinity of the distal end and engaging with tissue when placing the leadless pacemaker device on tissue with its distal end.

If the implantable medical device is a leadless pacemaker device, the housing provides for an encapsulation of the implantable medical device, the implantable medical device including all required components for autonomous operation, such as the processing circuitry, an energy storage such as a battery, electric and electronic circuitry and the like, within the housing. The housing is fluid-tight such that the implantable medical device may be implanted into cardiac tissue and may be kept in cardiac tissue over an extended period of time to provide for a long-term, continuous cardiac pacing operation.

In one embodiment, the start criterion is assumed to be fulfilled if a predefined multiplicity of signal samples of the cardiac sense signal is smaller than the start threshold. The processing circuitry hence is configured to monitor whether a predefined number of multiple signal samples are below the start threshold. Only if this is the case, the atrial detection window is started.

The multiplicity of signal samples herein may have to be consecutive or may not have to be consecutive. In particular, it may be monitored whether a predefined multiplicity of consecutive signal samples are below the start threshold. Only if such multiplicity of consecutive samples is detected, the atrial detection window is started. Alternatively, if the signal samples do not need to be consecutive, the atrial detection window is started once a (total) number of signal samples according to the predefined multiplicity of signal samples is found to be below the start threshold, independent of whether the signal samples are consecutive or not.

The number of signal samples that has to be below the start threshold in order to start the atrial detection window may, for example, lie in between 1 to 20, for example between 3 and 6, for example at 4.

The number of signal samples which need to be below the start threshold in order for the start criterion to be fulfilled may be programmable, such that a user may define number of samples by suitably programming the implantable medical device.

In one embodiment, the processing circuitry is configured to start the atrial detection window at the time of detection that the start criterion is fulfilled. The atrial detection window hence may be started immediately once the start criterion is found to be fulfilled. Hence, once it is detected that the pre-required number of signal samples is below the start threshold, the atrial detection window is started and it is monitored for signal deflections potentially indicative of an atrial event.

In another embodiment, the atrial detection window may not be immediately started at the time of detecting that the start criterion is fulfilled, but at a gap with respect to the time at which the start criterion has been fulfilled. The gap may be programmable.

In one embodiment, the processing circuitry is configured to blank a portion of said cardiac sense signal in a blanking window and to start monitoring the cardiac sense signal to detect whether the start criterion is fulfilled after the end of the blanking window. The blanking window generally serves to suppress such signal portions which likely are not due to atrial activity. In particular, the blanking window should cover, in an intracardiac electrogram, signal portions relating to a QRS waveform and a T wave, which stem from ventricular activity and hence generally exhibit large signal amplitudes. As signals relating to atrial activity may be much smaller in amplitude with respect to ventricular signal deflections, by means of the suppression of ventricular signal deflections a sensitivity for atrial signal deflections may be increased, and a waveform relating to atrial activity may be discerned from other signal portions.

The blanking window generally may be started in dependence of a detection of a prior ventricular event. The blanking window generally should be so long that a T wave in an intracardiac electrogram following a prior QRS waveform is reliably covered by the blanking window.

Once the blanking window has elapsed, it is started to monitor whether the start criterion is fulfilled. By means of the start criterion, herein, it is analyzed whether signal portions likely not relating to atrial activity have sufficiently decayed, and only if this is found—by comparing signal samples of the cardiac sense signal to the start threshold—the atrial detection window is started.

In one embodiment, the processing circuitry is configured to monitor the cardiac sense signal in a first processing state before the start criterion is fulfilled. Prior to starting the atrial detection window the cardiac sense signal in particular may be monitored in a non-processed fashion by not applying any particular signal processing. In order to assess the start criterion hence the raw signal data of the cardiac sense signal is examined.

In one embodiment, the processing circuitry is configured to monitor the cardiac sense signal in a second processing state within the atrial detection window for detecting a signal deflection of the cardiac sense signal potentially indicative of an atrial event. Once the atrial detection window is started, based on the checking of the start criterion, an atrial event is searched for based on the cardiac sense signal in a second processing state. In the second processing state the cardiac sense signal in particular may be processed, for example by applying a filtering, such as a bandpass filtering, a rectification, an averaging or the like in order to allow for a reliable detection of an atrial event based on signal deflections in the atrial detection window. Hence, once the atrial detection window is started a signal processing of the cardiac sense signal may be switched on, such that the cardiac sense signal in the atrial detection window is suitably processed in order to allow for a reliable detection of an atrial event.

In one embodiment, the processing circuitry is configured to detect a signal deflection in the cardiac sense signal potentially indicative of an atrial event within the atrial detection window based on a comparison of the cardiac sense signal to a sense threshold in the atrial detection window. An atrial event hence is detected by comparing the cardiac sense signal to the sense threshold, wherein an atrial event, for example, is assumed to be present if a crossing of the sense threshold based on one or multiple signal values is identified.

In one embodiment, the start threshold is equal to the sense threshold. In another embodiment, the start threshold may differ from the sense threshold.

In one embodiment, the processing circuitry is configured, if a signal deflection potentially indicative of an atrial event is identified, to determine a peak amplitude associated with the atrial event. Generally, if an atrial event is detected, an associated peak amplitude shall be determined in order to enable the setting, for example, of a sense threshold and potentially also the start threshold in a subsequent cardiac cycle. By dynamically adjusting the sense threshold and potentially also the start threshold based on the peak amplitude, the sense threshold and potentially also the start threshold may dynamically be adjusted, such that a checking of atrial events may be improved.

In one embodiment, at the time of detection of an atrial event, based on a crossing of the sense threshold by the cardiac sense signal in the atrial detection window, a peak detection window may be started. Within the peak detection window the cardiac sense signal is tracked in order to determine the maximum of the cardiac sense signal within the peak detection window. The maximum is then assumed to be the peak amplitude and is used for further processing.

Using the peak amplitude, the processing circuitry may be configured to compute the sense threshold for detecting an atrial event in a subsequent cardiac cycle. In particular, the processing circuitry may be configured to update the sense threshold using an average threshold reference and a percentage ratio according to the formula $$ST = PC \cdot ATR(t),$$

where ST is the current sense threshold, PC is a percentage ratio, and ATR(t) is the current average threshold reference for cycle t. The percentage ratio may lie, for example, in the range between 0% and 100%, in particular between 25% and 75%, and may be programmable.

In another embodiment, the average threshold reference may be computed based on the peak amplitude PA according to the following equation:

$$ATR(t) = W \cdot PA(t-1) + (1 - W) \cdot ATR(t-1),$$

where W indicates the update weight which determines how much the average threshold reference should change based on the previous peak amplitude, PA(t−1) is the peak amplitude as determined for the previous cycle t−1, and ATR(t−1) is the previous average threshold reference. For the actual cycle t the average threshold reference hence is determined based on the peak amplitude PA determined for that cycle t and based on the previously valid average threshold reference at cycle t−1. For each cycle for which an atrial event As is detected, hence, the average threshold reference is updated and computed anew, such that the average threshold reference is dynamically adjusted on a cycle-by-cycle basis.

The average threshold reference may, for example, be computed as a mean value of peak amplitudes for a predefined number of cardiac cycles in which atrial events have been detected, for example a number in between two to six cardiac cycles, for example four cardiac cycles.

In one embodiment, the processing circuitry comprises a first processing channel having a first gain for processing a first processing signal derived from sensor signals received via the sensor arrangement and a second processing channel having a second gain for processing a second processing signal derived from sensor signals received via the sensor arrangement, the second gain being higher than the first gain.

Generally, the implantable medical device may be configured to process different processing signals. For obtaining such processing signals, a sensor arrangement is provided, the sensor arrangement comprising e.g., one or multiple electrodes to receive electrical signals from which the processing signals are derived. The processing signals herein, for example, may be obtained each using a pair of electrodes, wherein for obtaining the different processing signals the same pair of electrodes or different pairs of electrodes may be used. In the first case, a single electrical signal, such as an intracardiac electrogram, may be obtained, from which different processing signals, namely the first processing signal and the second processing signal are derived for separate processing. In the latter case, separate electrical signals relating, for example, to a ventricular sensing signal and an atrial sensing signal (i.e., by applying a sensing optimized for atrial sensing) may be received in order to derive the first processing signal and the second processing signal from such different electrical signals, the different electrical signals, for example, being received using different pairs of electrodes of the sensor arrangement.

The different processing signals, in one embodiment, are processed in different processing paths of the processing circuitry. For this, the processing circuitry comprises a first processing channel for processing the first processing signal, the first processing signal relating, for example, to a near-field (in particular ventricular) sensing signal which, according to the placement of the implantable medical device, for example, in a ventricle of a patient's heart, may be large such that the first processing channel may exhibit a rather low gain.

In addition, the processing circuitry comprises a second processing channel for processing the second processing signal, which may relate, for example, to a far-field atrial sensing signal which, in case of a placement of the implantable medical device in the ventricle, may have a small amplitude, due to the distance between the location of implantation and the source of origin of the signals. In order to allow for a reliable processing of the second processing signal, the second processing channel exhibits a gain higher than the gain of the first processing channel, such that features relating to atrial activity may be suitably analyzed within the received signals.

Because, for a placement of the implantable medical device in, for example, the ventricle, atrial activity occurs in the far field, atrial events within a regular ventricular sensing signal (for example, obtained from a regular ventricular QRS sensing channel) may be hard to discern, as a P wave stemming from atrial activity may exhibit a small amplitude in relation to QRS and T waves. For this reason signal portions relating to far-field activity may be processed separately from signals relating to near-field activity within the second processing channel, such that within the second processing channel far-field events may be detected with increased reliability and enhanced timing precision.

The implantable medical device, in one aspect, is to be placed entirely or partially in the right or left ventricle.

In one aspect, the sensor arrangement is formed by an electrode arrangement, the electrode arrangement comprising a first electrode arranged in the vicinity of a tip of the body. The first electrode shall come to rest on cardiac tissue in an implanted state of the implantable medical device, such that the first electrode contacts cardiac tissue e.g., at a location effective for injecting a stimulating signal into cardiac tissue for provoking a pacing action, in particular a ventricular pacing.

In one aspect, the electrode arrangement comprises a second electrode formed by an electrode ring circumferentially extending about the body. Alternatively, the second electrode may, for example, be formed by a patch or another electrically conductive area formed on the body. The second electrode is placed at a distance from the tip of the body and hence at a distance from the first electrode arranged at the tip.

In one embodiment, the processing circuitry is configured to process, as said first processing signal, a first signal sensed between the first electrode and the second electrode. Such first signal may be denoted as near-field vector to be received between a pair of electrodes comprised of the first electrode and the second electrode. As the first electrode and the second electrode may, in one embodiment, be located at a rather close distance to each other, such pair of electrodes is predominantly suited to receive signals in close proximity to the implantable medical device, i.e., in the near-field region within the ventricle if the implantable medical device is implanted into the ventricle. The sense signal received in between the first electrode and the second electrode is provided to the first processing channel for processing in order to, for example, detect near-field (e.g., ventricular) events in the signal.

In one embodiment, the body comprises a remote location (e.g., the far end of a housing of a leadless pacemaker device) removed from the tip, the electrode arrangement comprising a third electrode arranged on the body at the remote location. The third electrode is operatively connected to the processing circuitry, such that the processing circuitry is enabled to receive and process signals received via the third electrode.

In one embodiment, the processing circuitry is configured to process, as said second processing signal, a second signal sensed between the first electrode and the third electrode. Such second signal vector arising between the first electrode and the third electrode may be referred to as far-field vector, the first electrode and the third electrode exhibiting a distance with respect to each other larger than the first and the second electrode. The second signal may in particular be processed to detect events in the far-field, i.e., atrial contractions in case the implantable medical device is placed in the ventricle, such that by means of the second signal an intrinsic atrial activity prior to injecting a pacing stimulus may be captured.

The second signal sensed between the first electrode and the third electrode may be used to sense intrinsic atrial contractions in order to provide for an atrial-to-ventricular synchronization by timely injecting a stimulus at the ventricular location of implantation of the pacemaker device following atrial contractions. The second signal is provided to the second processing channel in order to process the signal and detect atrial events from the signal, in order to provide for a pacing action based on detected atrial events, hence allowing for a ventricular pacing under atrioventricular (AV) synchrony.

In one embodiment, the second processing channel comprises a processing stage for differentiating one wave portion from another wave portion in the second processing signal.

The processing stage in particular may be configured to apply, to the second processing signal, at least one of a bandpass filtering, a blanking window for excluding a portion of the second sensor signal from further processing, a moving average filtering, and a rectification. By means of the processing stage, in particular such wave portions shall be isolated and/or emphasized within the signal to be processed which may be indicative of e.g., an atrial event. If the implantable medical device is placed in the ventricle of a patient's heart, signal portions relating to far-field atrial activity may have a much smaller amplitude than signal portions relating to a near-field ventricular activity. Hence, the processing serves to differentiate between the different signal portions in order to identify such signal portion which may contain signals relating to far-field atrial activity.

For isolating e.g., the P wave in an intracardiac electrogram, a bandpass filtering may be applied, hence differentiating wave portions relating to the P wave from wave portions in particular relating to QRS and T waves stemming from ventricular activity. Alternatively or in addition, other methods such as a moving average filtering, finite differences or a rectification of the signal may be applied. A moving averaging filter herein can be used to smooth the processing signal. Rectification can serve to easily compare the processed signal to a (single) threshold in order to identify when the signal magnitude exceeds a predefined threshold.

In another aspect, a method for operating an implantable medical device for providing for an intracardiac function comprises: receiving, using a sensor arrangement arranged on a body of the implantable medical device, q cardiac sense signal: and processing, using a processing circuitry operatively connected to the sensor arrangement, the cardiac sense signal received using the sensor arrangement to monitor the cardiac sense signal to detect whether a start criterion is fulfilled, wherein the start criterion is fulfilled if at least one signal sample of the cardiac sense signal is smaller than a start threshold, and to start an atrial detection window for detecting, within the atrial detection window, a signal deflection of the cardiac sense signal potentially indicative of an atrial event, based on whether said cardiac sense signal fulfills the detection criteria of exceeding the sense threshold for the programmed number of samples.

The advantages and advantageous embodiments described above for the device equally apply also to the method, such that is shall be referred to the above.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The various features and advantages of the present invention may be more readily understood with reference to the following detailed description and the embodiments shown in the drawings. Herein.

DETAILED DESCRIPTION

Figure 1:
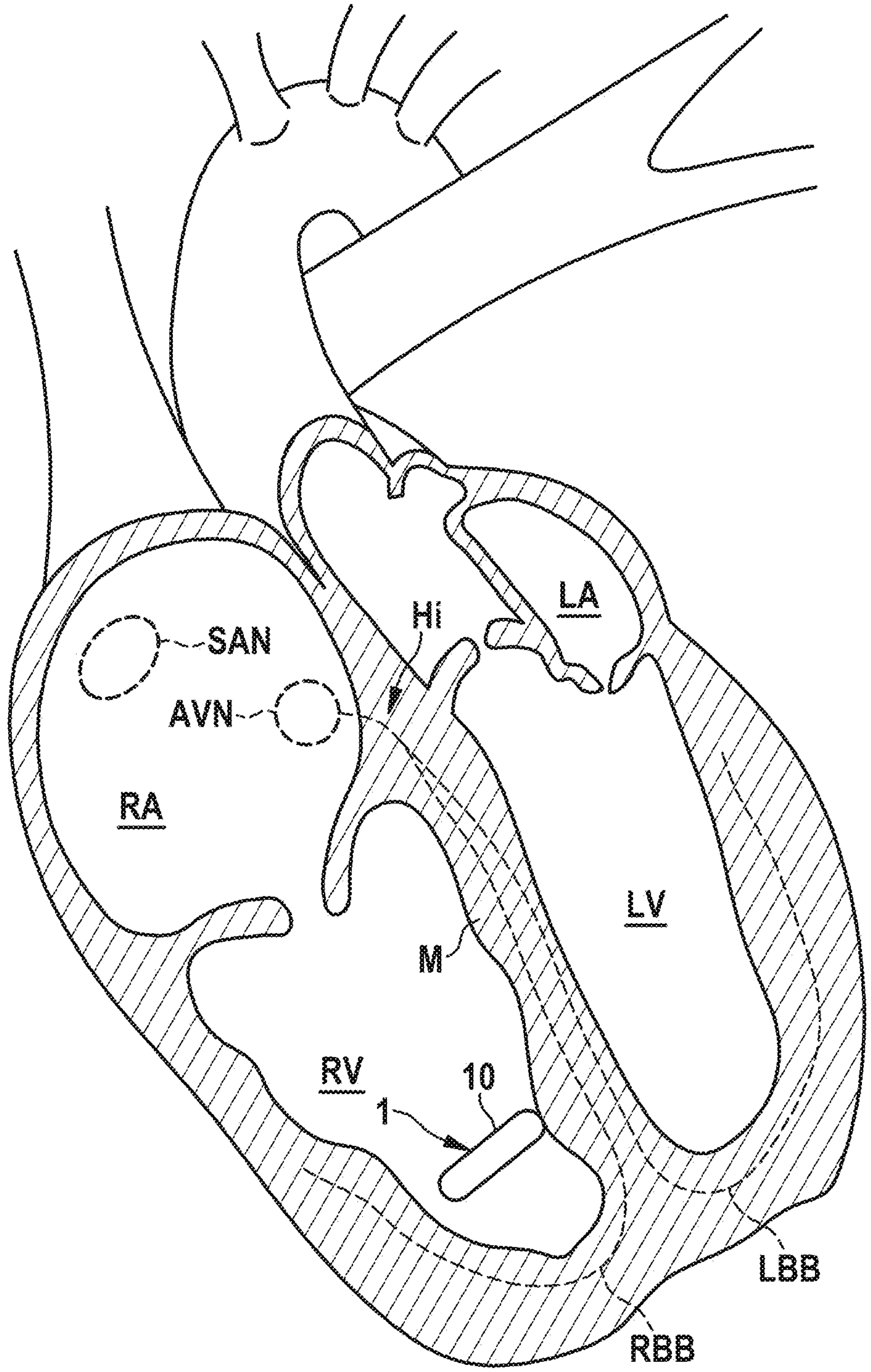
FIG. 1 shows a schematic view of the human heart, with an implantable medical device in the shape of a leadless pacemaker device implanted therein.

Subsequently, embodiments of the present invention shall be described in detail with reference to the drawings. In the drawings, like reference numerals designate like structural elements.

It is to be noted that the embodiments are not limiting for the present invention, but merely represent illustrative examples.

In the instant invention it is proposed to provide an implantable medical device providing for an intracardiac function, in particular a ventricular pacing, specifically a so-called VDD pacing.

FIG. 1 shows, in a schematic drawing, the human heart comprising the right atrium RA, the right ventricle RV, the left atrium LA and the left ventricle LV, the so-called sinoatrial node SAN being located in the wall of the right atrium RA, the sinoatrial node SAN being formed by a group of cells having the ability to spontaneously produce an electrical impulse that travels through the heart's electrical conduction system, thus causing the heart to contract in order to pump blood through the heart. The atrioventricular node AVN serves to coordinate electrical conduction in between the atria and the ventricles and is located at the lower back section of the intra-atrial septum near the opening of the coronary sinus. From the atrioventricular node AVN the so-called HIS bundle H is extending, the HIS bundle H being comprised of heart muscle cells specialized for electrical conduction and forming part of the electrical conduction system for transmitting electrical impulses from the atrioventricular node AVN via the so-called right bundle branch RBB around the right ventricle RV and via the left bundle branch LBB around the left ventricle LV.

In case of a block at the atrioventricular node AVN, the intrinsic electrical conduction system of the heart H may be disrupted, causing a potentially insufficient intrinsic stimulation of ventricular activity, i.e., insufficient or irregular contractions of the right and/or left ventricle RV, LV. In such a case, a pacing of ventricular activity by means of a pacemaker device may be indicated, such pacemaker device stimulating ventricular activity by injecting stimulation energy into intracardiac tissue, specifically myocardium M.

In one embodiment, an implantable medical device 1 in the shape of a leadless cardiac pacemaker device, as schematically indicated in FIG. 1, is provided ventricular pacing, the leadless pacemaker device having a body 10 formed by the housing of the leadless pacemaker device.

Figure 7:
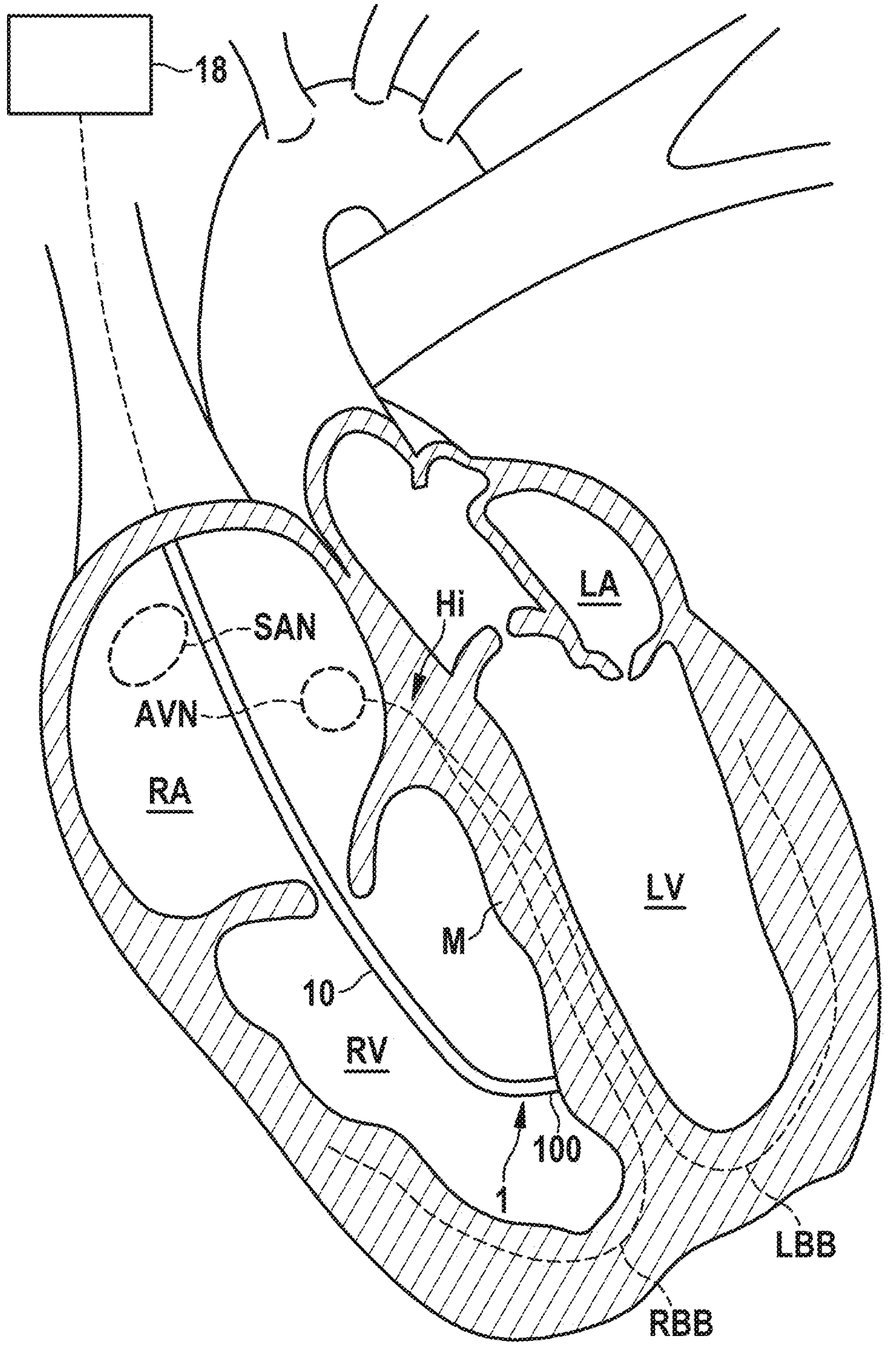
FIG. 7 shows a schematic view of the human heart, with an implantable medical device in the shape of cardiac stimulation device having a lead implanted in the right ventricle.

In another embodiment, as shown in FIG. 7, the implantable medical device 1 may be a stimulation device having a generator 18 and at least one lead forming a body 10 of the implantable medical device 1 and extending transvenously from the generator 18 into the patient's heart.

Whereas common implantable medical devices are designed to sense a ventricular activity by receiving electrical signals from the ventricle RV, LV they are placed in, it may be desirable to provide for a pacing action which achieves atrioventricular (AV) synchrony by providing a pacing in the ventricle in synchrony with an intrinsic atrial activity. For such pacing mode, also denoted as VDD pacing mode, it is required to sense atrial activity and identify atrial events relating to atrial contractions in order to base a ventricular pacing on such atrial events.

Figure 3:
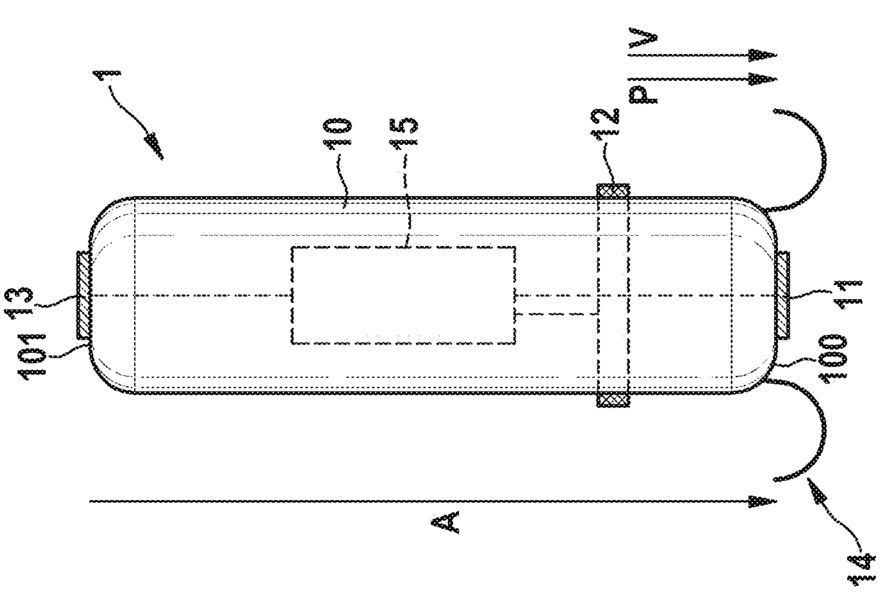
FIG. 3 shows a schematic view of an implantable medical device, indicating signal vectors between different electrodes of the implantable medical device.
Figure 2:
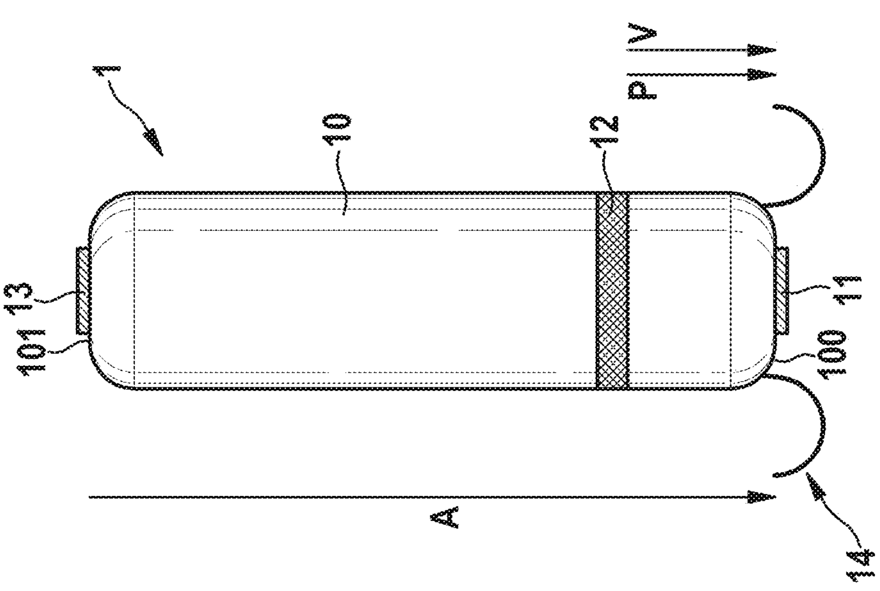
FIG. 2 shows a schematic view of an implantable medical device.

Referring now to FIGS. 2 and 3, in one embodiment an implantable medical device 1 in the shape of a leadless pacemaker device configured to provide for an intracardiac pacing, in particular in a VDD pacing mode, comprises a housing 10 enclosing electrical and electronic components for operating the implantable medical device 1. In particular, enclosed within the housing 10 is a processing circuitry 15, comprising, for example, also a communication interface for communicating with an external device, such as a programmer wand. In addition, electrical and electronic components such as an energy storage in the shape of a battery are confined in the housing 10. The housing 10 provides for an encapsulation of components received therein, the housing 10 having the shape of, e.g., a cylindrical shaft having a length of, for example, a few centimeters.

The implantable medical device 1 is to be implanted immediately on intracardiac tissue M. For this, the implantable medical device 1 comprises, in the region of a tip 100, a fixation device 14, for example, in the shape of nitinol wires to engage with intracardiac tissue M for fixedly holding the implantable medical device 1 on the tissue in an implanted state.

The implantable medical device 1 in the embodiment of FIGS. 2 and 3 does not comprise leads, but receives signals relating to a cardiac activity by means of an electrode arrangement arranged on the housing 10 and also emits stimulation signals by means of such electrode arrangement. In the embodiment of FIGS. 2 and 3, the implantable medical device 1 comprises different electrodes 11, 12, 13 making up the electrode arrangement and serving to emit pacing signals towards intracardiac tissue M for providing a pacing and to sense electrical signals indicative of a cardiac activity, in particular indicative of atrial and ventricular contractions.

A first electrode 11 herein is denoted as pacing electrode. The first electrode 11 is placed at a tip 100 of the housing 10 and is configured to engage with cardiac tissue M.

A second electrode 12 herein is denoted as pacing ring. The second electrode 12 serves as a counter-electrode for the first electrode 11, a signal vector P arising between the first electrode 11 and the second electrode 12 providing for a pacing vector P for emitting pacing signals towards the intracardiac tissue M.

In addition, the second electrode 12 serves as a sensing electrode for sensing signals, in particular relating to ventricular contractions, a signal vector V arising between the second electrode 12 and the first electrode 11, the signal vector V being denoted as near-field vector.

The second electrode 12 is placed at a distance from the first electrode 11 and, for example, has the shape of a ring extending circumferentially about the housing 10. The second electrode 12 is, for example, placed at a distance of about 1 cm from the tip 100 of the housing 10 at which the first electrode 11 is placed.

The implantable medical device 1, in the embodiment of FIGS. 2 and 3, in addition comprises a third electrode 13 placed at a far end 101 of the housing 10, the third electrode 13 serving as a sensing electrode for sensing signals indicative of cardiac activity in the far-field. In particular, a signal vector A arises between the third electrode 13 and the first electrode 11, the signal vector A picking up signals being indicative, for example, of atrial contractions and being denoted as far-field vector.

The electrodes 11, 12, 13 are in operative connection with the processing circuitry 15, the processing circuitry 15 being configured to cause the first electrode 11 and the second electrode 12 to emit a pacing signal for providing a stimulation at the ventricle. The processing circuitry 15 furthermore is configured to process signals received via the electrodes 11, 12, 13 to provide for a sensing of cardiac activity, in particular atrial and ventricular contractions.

If the implantable medical device 1 has the shape of a stimulation device comprising a generator 18 and a lead extending from the generator 18, as shown in the embodiment of FIG. 7, a similar electrode arrangement comprising, for example, three electrodes 11, 12, 13 may be arranged on a lead implanted in and extending into the right ventricle RV, as shown in FIG. 7, such that the above also applies to an embodiment of the implantable medical device 1 having a lead extending into the patient's heart. In this case, the processing circuitry may be part of the generator 18 and may be in operative connection with an electrode arrangement arranged on the lead.

In order to provide for a pacing in the ventricle in which the implantable medical device 1 is placed, in particular to enable a pacing in the VDD mode, a sensing of atrial activity is required to provide for detected atrial sense markers in order to time a pacing in the ventricle to obtain atrioventricular (AV) synchrony. For this, a far-field signal from in particular the right atrium RA (see FIGS. 1 and 9) shall be sensed in order to allow for a synchronous pacing in the right ventricle RV by means of the implantable medical device 1 being implanted on intracardiac tissue M in the right ventricle RV.

Figure 4:
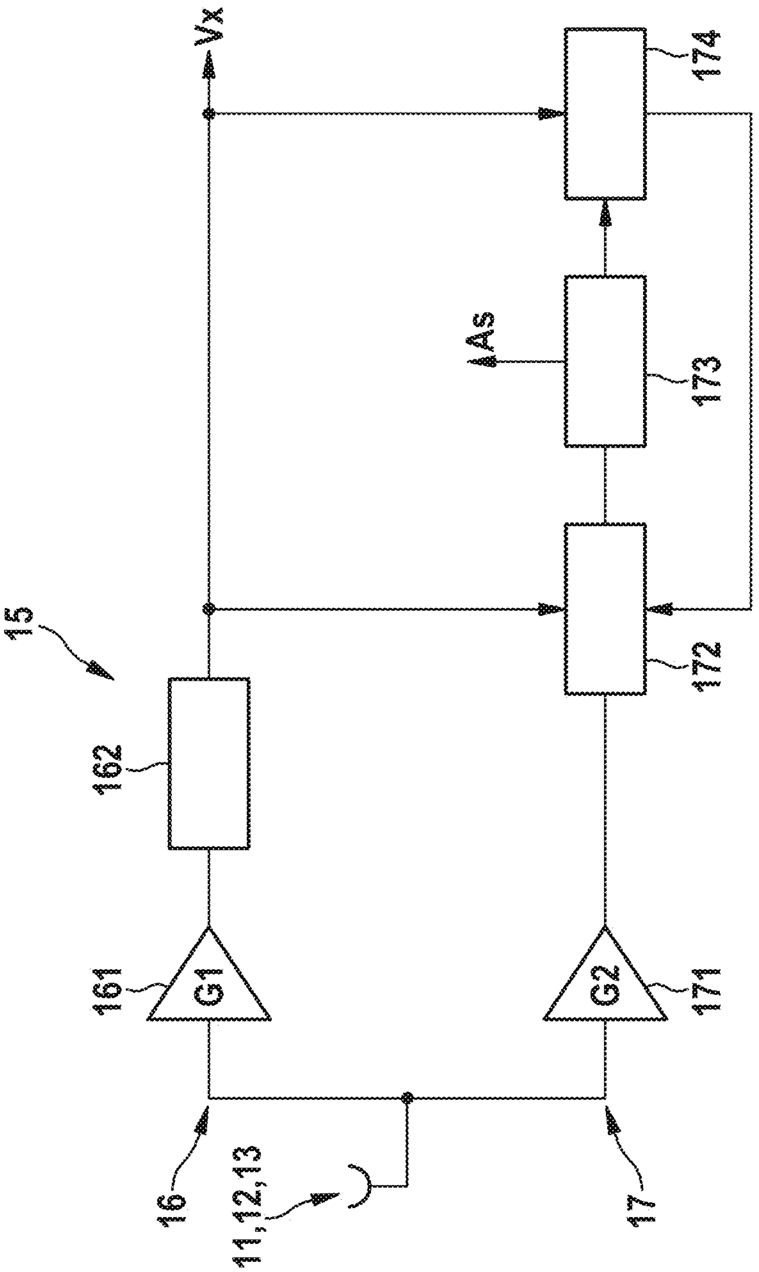
FIG. 4 shows a schematic view of a processing circuitry of an embodiment of an implantable medical device.

Referring now to FIG. 4, the processing circuitry 15 comprises, in one embodiment, two processing channels 16, 17 for processing different processing signals relating to ventricular activity and atrial activity. Herein, typically, an intracardiac electrogram (IEGM) contains a signal portions relating to ventricular activity (in particular a QRS wave) and atrial activity (in particular a P wave), signal portions relating to atrial activity however resulting from a far-field signal source and hence being far less pronounced and having a far smaller amplitude then signal portions relating to a ventricular activity in the near-field, i.e., arising in close proximity to the implanted implantable medical device 1. For this reason, the two processing channels 16, 17 are associated with different gains G1, G2, a first processing channel 16 serving to process a first processing signal to identify ventricular events Vx at a rather low gain G1 and a second processing channel 17 being configured to process a second processing signal to identify atrial events at a significantly higher gain G2.

In particular, the first processing channel 16 is connected to the electrode arrangement comprised of the electrodes 11, 12, 13, the first processing channel 16 being configured in particular to sense and process a signal received via the electrodes 11, 12 (near-field vector V in FIGS. 2 and 3). The first processing channel 16 comprises a first amplification stage 161 having a gain G1, the first amplification stage 161 being follow by a detection stage 162 which is configured to identify ventricular sense markers Vx from the first processing signal processed within the first processing channel 16.

The second processing channel 17 is likewise connected to the electrode arrangement comprised of electrodes 11, 12, 13, wherein the second processing channel 17 may in particular be configured to process a signal sensed via the far-field vector A, that is in between the electrodes 11, 13 placed at the tip 100 and the far end 101 of the housing 10 as illustrated in FIGS. 2 and 3. The second processing channel 17 comprises a second amplification stage 171 having a second gain G2, the second amplification stage 171 being followed by a processing stage 172 and a second detection stage 173.

The processing stage 172 serves to pre-process the second processing signal after amplification. The detection stage 173 in turn serves to evaluate and analyze the processed signal in order to identify atrial events within the second processing signal, the second processing channel 17 then outputting atrial sense markers As indicative of atrial events detected in the processed signal.

In addition, the processing circuitry 15 comprises a timing stage 174 which uses timing information received from the first processing channel 16 and the second processing channel 17 to provide for a pacing timing, in particular a VDD timing for achieving an atrial-ventricular synchronous pacing.

In order to identify and analyze atrial events, the gain G2 of the second processing channel 17 is (significantly) higher than the gain G1 of the first processing channel 16. This generally allows to analyze signal portions relating to atrial events, but makes it necessary to discern such signal portions relating to atrial events from other signal portions, in particular signal portions relating to ventricular events Vx in the near-field and hence being far larger than signal portions originating from atrial events in the far-field.

Within the processing stage 172, for example a bandpass filtering, a windowing (e.g., partial blanking), a smoothing by means of a moving average filtering and a rectification may take place. A first or second order difference may be applied to remove a non-zero baseline while enhancing P wave defections.

Figure 5A:
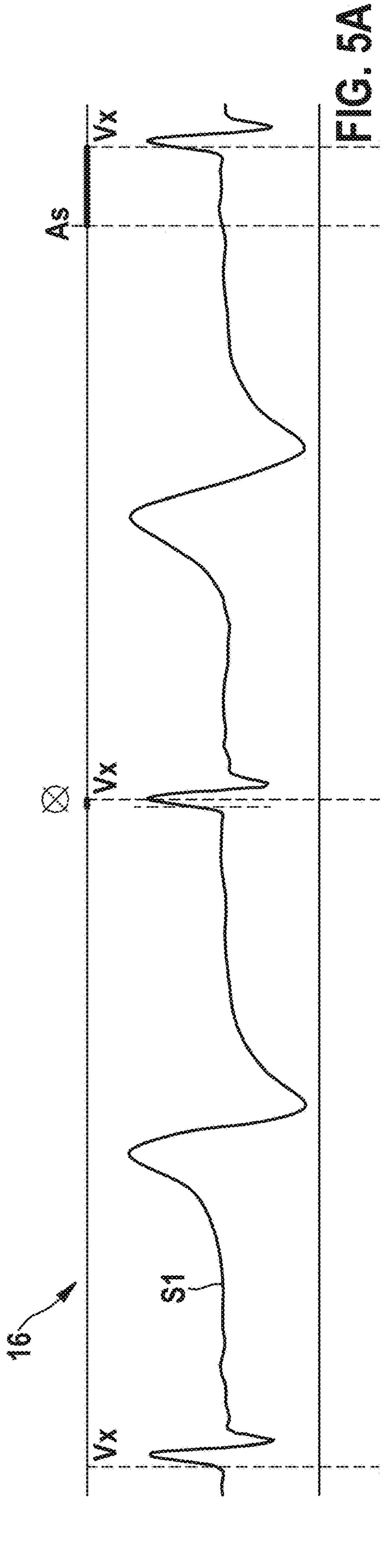
FIG. 5A shows a first processing signal in the shape of an intracardiac electrogram (IEGM) processed by a first processing channel of the processing circuitry.
Figure 5B:
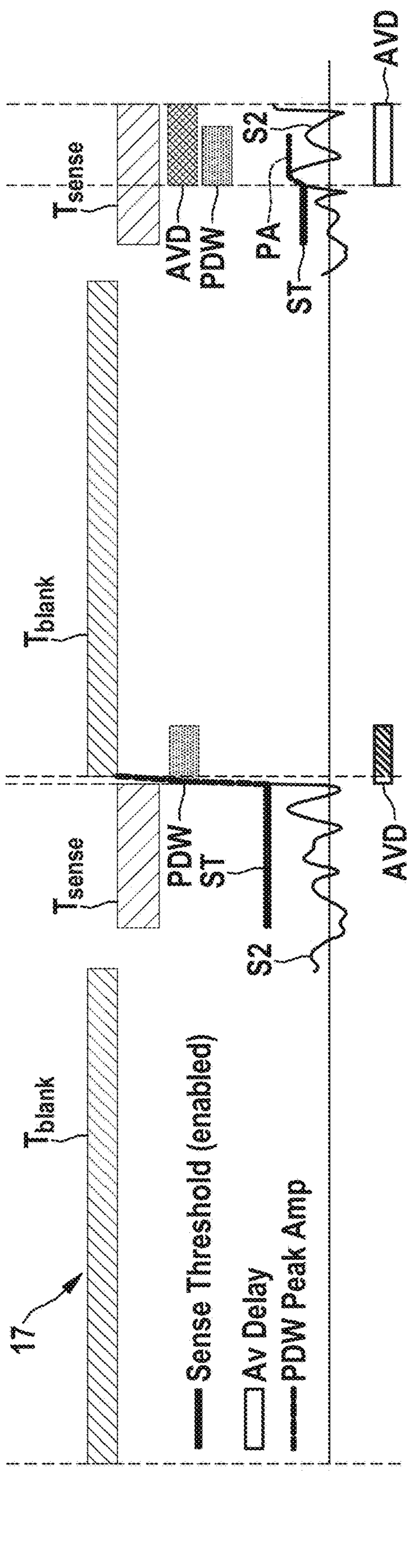
FIG. 5B shows a second processing signal processed by a second processing channel of the processing circuitry.

FIGS. 5A and 5B show examples of signals S1, S2 as processed in the different processing channels 16, 17, FIG. 5A at the top showing a signal S1 as processed by the first processing channel 16 and FIG. 5B at the bottom showing a signal S2 as processed by the second processing channel 17. As a result of the processing, ventricular events Vx and atrial events As are identified and corresponding markers are output.

As apparent from FIG. 5B, the sensing of atrial events As uses a windowing scheme, employing in particular a blanking window $T_{blank}$ for blanking out signal portions of the signal S2 potentially relating to ventricular activity.

In particular, by means of the detection of ventricular events Vx in the first processing channel 16 an (expected) timing in between atrial events As and ventricular events Vx may be determined. According to such timing a start point and an end point of the blanking window $T_{blank}$ may be set, hence excluding signal portions from the processing which do not relate to atrial activity. Large ventricular signals in this way may be suppressed such that signal portions relating to a ventricular activity may not interfere with a detection of atrial events.

During the blanking window $T_{blank}$, the second processing channel 17 may be turned off. In particular, the amplification stage 171 of the second processing channel 17 may be switched off in order to save power.

Generally, a detection for atrial events As takes place outside of the blanking window $T_{blank}$. As it shall be explained further below with reference to FIG. 6, an atrial detection window $T_{sense}$ is started after lapse of the blanking window $T_{blank}$, the atrial detection window $T_{sense}$ being started adaptively based on the cardiac sense signal S2 and a start criterion which takes into account whether signal portions likely not relating to atrial activity have sufficiently decayed after the end of the blanking window $T_{blank}$.

An atrial event As is assumed to be present if, in the atrial detection window $T_{sense}$, the signal S2 crosses a sense threshold ST, as it is shown in FIG. 5B. The comparison may take place based on a rectification of the sense signal S2. Alternatively, a positive and negative sense threshold ST may be used, which may have the same value or may differ in their values. A threshold crossing herein may be assumed if one signal value is larger than the sense threshold ST. Alternatively, a crossing of the sense threshold ST is assumed if a predefined number of signal values are larger than the sense threshold ST, for example two or more consecutive or non-consecutive sample values.

If an atrial event As is detected, as it is the case for the second cardiac cycle in FIG. 5B, the atrial event As is used for a further processing, in particular to update the sense threshold ST and to achieve an atrial-ventricular synchronous pacing.

In particular, the atrial event As is taken as that point in time at which a crossing of the sense threshold ST is identified. At the time of the atrial event As a peak detection window PDW starts, and based on data recorded during that peak detection window PDW a peak amplitude PA is determined as the maximum signal value within the peak detection window PDW. This is indicated in FIG. 5B.

Also, in case of a detection of an atrial event As, an atrial-ventricular delay AVD may be determined and used for subsequent processing. If no ventricular event Vx is detected after lapse of the atrial-ventricular delay AVD, a pacing signal may be injected to cause a ventricular stimulation.

As it is shown in FIG. 5B, the peak amplitude PA is determined within a peak detection window PDW following the detection of an atrial event As. Generally, the peak amplitude PA herein is determined by tracking the sense signal S2 and by in this way identifying the maximum of the sense signal S2 in the peak detection window PDW.

The peak amplitude PA is determined during a peak detection window PDW after the atrial event As (and/or its detection). As shown in FIG. 5B (and also FIG. 6) the peak detection window PDW may be during the atrial detection window $T_{sense}$. Therefore, the peak amplitude PA may be determined during the atrial detection window $T_{sense}$ and is not necessarily determined during a blanking window $T_{blank}$. Thus, in one embodiment, the peak amplitude PA is determined within the atrial detection window $T_{sense}$ and within a peak detection window PDW following the detection of an atrial event As.

The peak amplitude PA, in one embodiment, may be used to update the sense threshold ST for the next cardiac cycle.

In particular, the processing circuitry 15 may be configured to update the sense threshold ST using an average threshold reference and a percentage ratio according to the formula $$ST = PC \cdot ATR(t),$$

where ST is the current sense threshold, PC is the percentage ratio, and ATR(t) is the average threshold reference for the current cycle t. The percentage ratio may lie, for example, in the range between 0% and 100%, in particular between 25% and 75%.

In another embodiment, the average threshold reference may be computed based on the peak amplitude PA according to the following equation:

$$ATR(t) = W \cdot PA(t-1) + (1-W) \cdot ATR(t-1),$$

where W indicates the update weight which determines how much the average threshold reference should change based on the previous peak amplitude, PA(t−1) is the peak amplitude as determined for the previous cycle t−1, and ATR(t−1)

is the previous average threshold reference. For the actual cycle t the average threshold reference hence is determined based on the peak amplitude PA determined for that cycle t and based on the previously valid average threshold reference at cycle t−1. For each cycle for which an atrial event As is detected, hence, the average threshold reference is updated and computed anew, such that the average threshold reference is dynamically adjusted on a cycle-by-cycle basis.

The average threshold reference may, for example, be determined based on a mean value for a number of previous cardiac cycles in which atrial events have been identified and correspondingly peak amplitude values have been obtained. The average threshold reference in this case, for example, may be determined as the average of the peak amplitude values in the previous cardiac cycles.

If no (valid) atrial event As is detected, no peak amplitude PA is determined and the average threshold reference ATR is not updated. In this way it is avoided that a false detection of an atrial event As may cause a false increase of the sense threshold ST and a subsequent loss of accurate atrial detections. This is the case for the first cardiac cycle as shown in FIGS. 5A and 5B, in which no crossing of the sense threshold ST is detected and correspondingly no atrial event As is identified.

Figure 6:
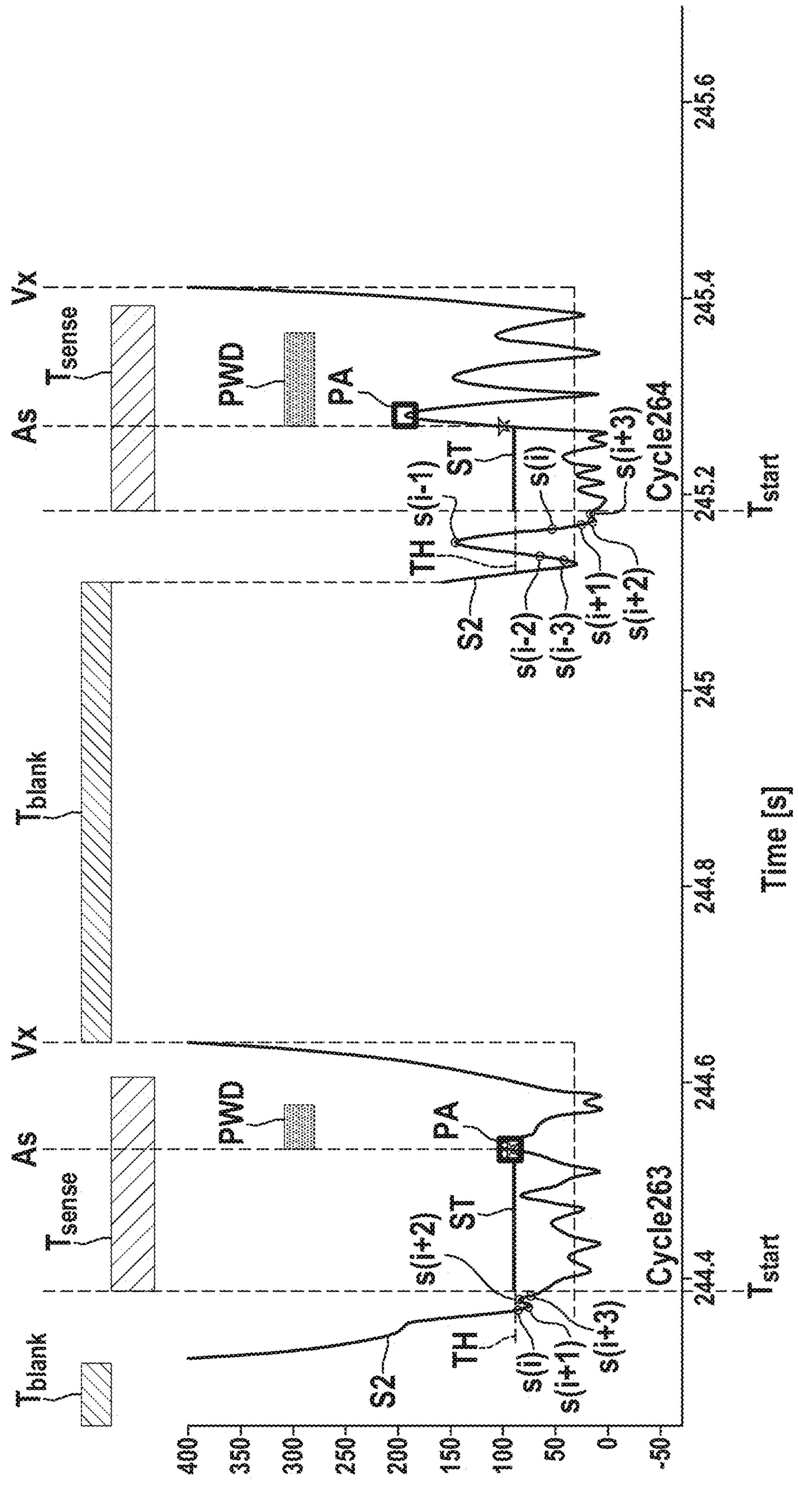
FIG. 6 shows an example of a second processing signal within two cardiac cycles.

Referring now to FIG. 6, the atrial detection window $T_{sense}$ generally shall cover those portions of the cardiac sense signal S2 (as processed in the second processing channel 17 of the processing circuitry 15 as illustrated in FIG. 4) which likely are related to atrial activity. Those signal portions which do not relate to atrial activity shall be excluded from the atrial detection window $T_{sense}$.

For this reason, in the embodiment of FIG. 6 the atrial detection window $T_{sense}$ is started adaptively based on the evaluation of a start criterion following the end of the blanking window $T_{blank}$.

As it is visible from FIG. 6, illustrating two subsequent cardiac cycles, an end of a preceding waveform, in particular a T wave in an intracardiac electrogram, may extend beyond the end of the blanking window $T_{blank}$ and may reach into a signal portion of the cardiac sense signal S2 relating to atrial activity. This in particular is apparent from the first cardiac cycle as shown in FIG. 6 on the left, in which a tail of a preceding waveform is present after the end of the blanking window $T_{blank}$. This also is visible in the second cardiac cycle as shown in FIG. 6 on the right, in which a peak likely relating to a prior T wave occurs after the end of the blanking window $T_{blank}$.

For this reason, the atrial detection window $T_{sense}$ is started only if a start criterion is fulfilled, for which it is checked whether a predefined number of signal samples of the cardiac sense signal are below a start threshold TH.

For the start criterion to be fulfilled it herein may be sufficient if one signal sample is below the start threshold TH. In another embodiment it may be required that more than one signal sample is smaller than the start threshold TH, for example 2, 3, 4 or more signal samples.

For the start criterion to be fulfilled it may be checked whether a predefined multiplicity of consecutive signal samples are smaller than the start threshold TH. Only if this is the case, the start criterion is assumed to be true. In another embodiment, the signal samples do not need to be consecutive in order for the start criterion to be fulfilled, but it is checked whether a total number of signal samples is smaller than the start threshold TH.

In the embodiment of FIG. 6, it is assumed that the start criterion is fulfilled if a predefined number of consecutive signal samples (in the shown example four signal samples) is found to be smaller than the start threshold TH. The number of signal samples herein may be programmable, wherein it also may be programmable whether the signal samples need to be consecutive or not for fulfilling the start criterion.

In the cardiac cycle in FIG. 6 on the left, at time $T_{start}$ it is found that four consecutive signal samples s(i) . . . s(i3) are below the start threshold TH. Hence, the start criterion is fulfilled, and the atrial detection window $T_{sense}$ is started.

In the subsequent cardiac cycle, in FIG. 6 on the right, two signal samples s(i−3), s(i−2) are found to be below the start threshold TH. A subsequent signal sample s(i−1) however lies above the start threshold TH, such that the count for consecutive signal samples below the start threshold TH is started anew. Only at time $T_{start}$ it is found that four consecutive signal samples s(i) . . . s(i+3) are smaller than the start threshold TH, upon which the atrial detection window $T_{sense}$ is started and the detection of an atrial event is initiated using a detection scheme as described above with reference to FIGS. 5A and 5B.

The atrial detection window $T_{sense}$ may be started immediately at the time $T_{start}$ at which the start criterion is found to be fulfilled. However, there also may be a gap in-between the time $T_{start}$ and the start of the atrial detection window $T_{sense}$.

The start threshold TH may be equal to the sense threshold ST as subsequently applied for detecting an atrial event in the atrial detection window $T_{sense}$, such that the start threshold TH may be set to the sense threshold ST as determined, for example, according to the scheme described above. In another embodiment, the start threshold TH may differ from the sense threshold ST, for example by a predefined factor.

In another embodiment the start threshold TH is programmed to a fixed value, which is not adapted cycle-to-cycle or related to the sense threshold ST. Further, the start threshold TH may be unequal to the sense threshold ST.

Using atrial sense markers As output by the processing circuitry 15, a ventricular synchronous pacing may be achieved. For this, it can be detected whether, following a detected atrial sense marker As, an intrinsic ventricular sense marker Vx occurs within a predefined time delay window (corresponding to the atrial-ventricular delay AVD) after the atrial sense marker As, in which case no stimulation is required. If no ventricular sense marker Vx is detected, a stimulation pulse may be emitted, causing a synchronous pacing at the ventricle.

Conversely, also an asynchronous pacing can be performed.

Utilizing a far-field electrical signal received by means of an implantable medical device can offer a superior detection of far-field events, in particular atrial events in case the implantable medical device is implanted into the ventricle. A tracking of far-field events by using and evaluating electrical signals may allow for an increased consistency and reliability in particular with respect to external factors such as posture and patient activity.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 Implantable medical device
10 Body (housing)
100 Tip
101 Far end
11 First electrode (pacing electrode)
12 Second electrode (pacing ring)
13 Third electrode
14 Fixation device
15 Processing circuitry
16 Processing channel
161 Amplification stage
162 Detection stage
17 Processing channel
171 Amplification stage
172 Processing stage
173 Detection stage
174 Timing stage
18 Generator
A Signal vector (atrial/far-field vector)
As Atrial event (atrial sense marker)
AVD Atrial-ventricular delay
AVN Atrioventricular node
G1, G2 Gain
H HIS bundle
LA Left atrium
LAT Lower absolute threshold
LBB Left bundle branch
LV Left ventricle
M Intracardiac tissue (myocardium)
P Signal vector (pacing vector)
PA Peak amplitude
PDW Peak detection window
RA Right atrium
RBB Right bundle branch
RV
Right ventricle
s(i−3) . . . s(i+3) Signal samples
S1, S2 Signal
SAN Sinoatrial node
ST Sense threshold
$T_{blank}$ Blanking window
$T_{sense}$ Detection window
$T_{start}$ Start time
TH Start threshold
V Signal vector (ventricular/near-field vector) V
Vx Ventricular event (ventricular sense marker) Vx

The invention claimed is:

1. A leadless pacemaker device configured to provide for an intracardiac function, the implantable medical device comprising:

a body formed by a housing of the leadless pacemaker device;

a sensor arrangement arranged on the body and configured to receive a cardiac sense signal; and a processing circuitry operatively connected to the sensor arrangement, wherein the processing circuitry is configured to process the cardiac sense signal received using the sensor arrangement:

to monitor the cardiac sense signal to detect whether a start criterion is fulfilled, wherein the start criterion is fulfilled if at least one signal sample (s(i−3) . . . s(i+3)) of the cardiac sense signal is smaller than a start threshold; and to start an atrial detection window for detecting, within the atrial detection window, a signal deflection of the cardiac sense signal indicative of an atrial event, based on whether said start criterion is fulfilled;

wherein the processing circuitry is configured to detect the signal deflection in the cardiac sense signal indicative of an atrial event based on a comparison of the cardiac sense signal to a sense threshold in the atrial detection window, wherein the processing circuitry is configured to adjust a pacing function of the leadless pacemaker device based on the detected signal deflection.

2. The leadless pacemaker device according to claim 1, wherein the start criterion is fulfilled if a predefined multiplicity of signal samples (s(i−3) . . . s(i+3)) of the cardiac sense signal is smaller than the start threshold.

3. The leadless pacemaker device according to claim 1, wherein the start criterion is fulfilled if a predefined multiplicity of consecutive signal samples (s(i−3) . . . s(i+3)) of the cardiac sense signal is smaller than the start threshold.

4. The leadless pacemaker device according to claim 2, wherein the predefined multiplicity of signal samples (s(i−3) . . . s(i+3)) lies in a range between 1 and 20.

5. The leadless pacemaker device according to claim 1, wherein the processing circuitry is configured to start the atrial detection window at the time of detection that the start criterion is fulfilled.

6. The leadless pacemaker device according to claim 1, wherein the processing circuitry is configured to blank a portion of said cardiac sense signal in a blanking window and to start monitoring the cardiac sense signal to detect whether the start criterion is fulfilled after the end of the blanking window.

7. The leadless pacemaker device according to claim 1, wherein the processing circuitry is configured to monitor the cardiac sense signal in a first processing state before the start criterion is fulfilled.

8. The leadless pacemaker device according to claim 1, wherein the processing circuitry is configured to monitor the cardiac sense signal in a second processing state within the atrial detection window for detecting the signal deflection of the cardiac sense signal indicative of an atrial event.

9. The leadless pacemaker device according to claim 1, wherein the start threshold is equal to the sense threshold.

10. The leadless pacemaker device according to claim 1, wherein the processing circuitry is configured, if the signal deflection indicative of an atrial event is detected, to determine a peak amplitude associated with the atrial event.

11. The leadless pacemaker device according to claim 10, wherein the processing circuitry is configured to determine the peak amplitude associated with the atrial event in a peak detection window following the atrial event (As).

12. The leadless pacemaker device according to claim 1, wherein the processing circuitry comprises a first processing channel having a first gain for processing a first processing signal derived from cardiac sense signals received via the sensor arrangement and a second processing channel having a second gain for processing a second processing signal derived from cardiac sense signals received via the sensor arrangement, the second gain being higher than the first gain.

13. Method for operating a leadless pacemaker device for providing for an intracardiac function, comprising:

receiving, using a sensor arrangement arranged on a body of the implantable medical device, a cardiac sense signal;

processing, using a processing circuitry operatively connected to the sensor arrangement, the cardiac sense signal received using the sensor arrangement:

to monitor the cardiac sense signal to detect whether a start criterion is fulfilled, wherein the start criterion is fulfilled if at least one signal sample (s(i−3) . . . s(i+3)) of the cardiac sense signal is smaller than a start threshold; and to start an atrial detection window for detecting, within the atrial detection window, a signal deflection of the cardiac sense signal indicative of an atrial event, based on whether said start criterion is fulfilled, detecting the signal deflection in the cardiac sense signal indicative of an atrial event based on a comparison of the cardiac sense signal to a sense threshold in the atrial detection window, and adjusting a pacing function of the leadless pacemaker device based on the detected signal deflection.

* * * * *